United States Patent [19]
Warman et al.

[11] Patent Number: 5,922,014
[45] Date of Patent: Jul. 13, 1999

[54] SINGLE PASS LEAD AND METHOD OF USE

[75] Inventors: Eduardo N. Warman, Maple Grove; Matthew D. Bonner, Plymouth, both of Minn.

[73] Assignee: Medtronic, Inc., Minneapolis, Minn.

[21] Appl. No.: 08/922,693

[22] Filed: Sep. 2, 1997

[51] Int. Cl.⁶ ........................................... A61N 1/05
[52] U.S. Cl. ................... 607/123; 607/122; 607/126; 607/125
[58] Field of Search ............................. 600/374, 375; 607/119, 122, 123, 125, 126, 128

[56] References Cited

U.S. PATENT DOCUMENTS

| | | |
|---|---|---|
| 3,729,008 | 4/1973 | Berkovits . |
| 3,825,015 | 7/1974 | Berkovits . |
| 3,865,118 | 2/1975 | Bures . |
| 3,903,897 | 9/1975 | Woollons et al. . |
| 4,030,508 | 6/1977 | Thalen . |
| 4,033,357 | 7/1977 | Helland et al. . |
| 4,355,646 | 10/1982 | Kallok et al. . |
| 4,386,615 | 6/1983 | Sowton . |
| 4,394,866 | 7/1983 | Hughes . |
| 4,401,126 | 8/1983 | Reenstierna . |
| 4,402,329 | 9/1983 | Williams . |
| 4,402,330 | 9/1983 | Lindemans . |
| 4,497,326 | 2/1985 | Curry . |
| 4,506,680 | 3/1985 | Stokes . |
| 4,627,439 | 12/1986 | Harris . |
| 4,934,381 | 6/1990 | MacGregor . |
| 4,972,848 | 11/1990 | DiDomenico et al. . |
| 5,235,977 | 8/1993 | Hirschberg et al. . |
| 5,269,298 | 12/1993 | Adams et al. . |
| 5,282,844 | 2/1994 | Stokes et al. . |
| 5,303,704 | 4/1994 | Molacek et al. . |
| 5,324,321 | 6/1994 | Pohndorf et al. . |
| 5,411,546 | 5/1995 | Bowald et al. . |
| 5,423,865 | 6/1995 | Bowald et al. ........................ 607/126 |
| 5,431,683 | 7/1995 | Bowald et al. . |
| 5,584,873 | 12/1996 | Shobert et al. . |
| 5,628,778 | 5/1997 | Kruse et al. . |
| 5,628,779 | 5/1997 | Bornzin et al. . |
| 5,643,338 | 7/1997 | Bornzin et al. ........................ 607/125 |
| 5,772,693 | 6/1998 | Brownlee ............................... 607/126 |

FOREIGN PATENT DOCUMENTS

| | | |
|---|---|---|
| 0601338 | 6/1994 | European Pat. Off. . |
| 0606688 | 7/1994 | European Pat. Off. . |
| 0788808 | 2/1997 | European Pat. Off. . |

OTHER PUBLICATIONS

"Toward Optimizing a Preshaped Catheter and System Parameters to Achieve Single Lead DDD Pacing", by Brownlee et al, published in *PACE*, May 1997, Part I, pp. 1354–1358.

"Penetration of Atrial Myocardium into the Vena Cavae" by Schwartzman et al, Published in *PACE*, Apr. 1997, Part II, p. 1202.

*Primary Examiner*—William E. Kamm
*Assistant Examiner*—George R. Evanisko
*Attorney, Agent, or Firm*—Reed A. Duthler; Harold R. Patton

[57] ABSTRACT

A cardiac pacing lead for pacing the atria and a method of its use. The lead is provided with a mechanism for maintaining an atrial pacing electrode adjacent stimulable tissue in a patient's superior vena cava and an additional electrode locatable in the right ventricle or elsewhere when the atrial electrode is so located. One such mechanism for maintaing the atrial electrode's position may be a lead body displaying pre-formed laterally extending curves sized to span a patient's superior vena cava, with the atrial electrode located thereon.

10 Claims, 9 Drawing Sheets

SINGLE PASS LEAD AND METHOD OF USE

BACKGROUND OF THE INVENTION

The present invention relates generally to implantable electrical leads and more particularly implantable single pass cardiac pacing leads.

It has long been a goal to provide a single cardiac lead which will reliably sense and pace both the atrium and ventricles of a human heart. The simplest approach to providing such lead is simply to add one or more electrodes to the body of a ventricular pacing lead spaced from the distal end of the lead a distance appropriate to locate the added electrodes in the atrium. Such leads are disclosed in U.S. Pat. No. 3,903,897 issued to Woollons and U.S. Pat. No. 3,825,015 issued to Berkovits. While such leads have been proven to sense reliably in the atrium and are currently used in conjunction with VDD pacemakers, their ability to reliably pace the atria is less than might be desired.

Over the years, numerous designs have been proposed and tested which attempted to provide for reliable positioning of the atrial electrodes on a single pass lead adjacent the tissue of the atria in order to allow for reliable cardiac pacing. These approaches have included the provision of active fixation electrodes for use in the atrium as disclosed in U.S. Pat. No. 4,402,329 issued to Williams and U.S. Pat. No. 4,497,326 issued to Curry and the provision of expandable or extendable arms as in U.S. Pat. No. 3,865,118 issued to Bures and U.S. Pat. No. 4,386,615 issued to Sowton.

One of the most common proposals for locating an electrode in the atrium in the context of a single pass lead is the provision of pre-formed loops, coils, or other laterally extending curves formed in the lead body to assist in maintaining an electrode located thereon adjacent the tissue of the atrium. Such leads include U.S. Pat. No. 5,628,778 issued to Kruse et al., U.S. Pat. No. 4,401,126 issued to Reenstierna and U.S. Pat. No. 4,627,439 issued to Harris.

It has also been suggested that an atrial electrode may be stabilized by provision of pre-formed curves, loops or coils proximal to the electrode, intended to be located in the superior vena cava. Such leads are disclosed in U.S. Pat. No. 4,394,866 issued to Hughes and U.S. Pat. No. 5,628,779 issued to Bornzin et al. and in the article "Toward Optimizing a Preshaped Catheter and System Parameters to Achieve Single Lead DDD Pacing", by Brownlee et al., published in *Pace,* May 1997, Part I, pp. 1354–1358.

SUMMARY OF THE INVENTION

The present invention is directed toward the provision of a workable single pass lead which is easy to implant, and provides an opportunity for reliably pacing the right atrium in conjunction with providing stimulus or cardioversion/defibrillation pulses to a second location in or near the heart and toward a method of using the lead.

The present invention accomplishes these goals by means of a lead configured to allow simultaneous location of a pacing and/or defibrillation electrode at the right ventricular apex or elsewhere and location of atrial stimulation electrodes in the superior vena cava. In this context, as reflected in the article "Penetration of Atrial Myocardium into the Vena Cavae", by Schwartzman et al., Published in *Pace,* April 1997, Part II, p. 1202 it should be understood that stimulable tissue from the atrium may extend up to 3 centimeters into this superior vena cava. This fact offers unique opportunities in the context of single pass AV pacing leads and is employed by the present invention to provide an improved, easy to use single-pass lead. The superior vena cava remains relatively motionless during the beating of the heart, the motion of the heart. As such it is possible to locate an atrial electrode using non-active fixation mechanisms such as loops or coils in a stable location in the superior vena cava with substantially greater success than employing these mechanisms located adjacent the wall of the right atrium. A lead according to one embodiment of the present invention can therefore be provided with a series of laterally extending loops or coils sized to maintain the lead located in the superior vena cava, hereafter referred to as "fixation curves" and may be provided with one or more electrodes mounted along the fixation curves in positions such that at least one of the electrodes will be in contact with the tissue of the superior vena cava in a position which allows for reliable atrial pacing.

In a preferred embodiment of the invention, order to further reduce the likelihood of displacement, the lead body may further be provided with a series of curves extending laterally to a lesser extent than the fixation curves, hereafter referred to as "stretch curves", located proximally and/or distally to the fixation curves in order to prevent tensile forces applied to the lead proximally and/or distally to the fixation curves from dislodging the atrial pacing electrodes. In a preferred embodiment, the lead body may also be made more flexible and pliant proximal and distal to the portion to be located in the superior vena cava.

The lead may carry one or more atrial pacing electrodes for location in the superior vena cava in conjunction with one or more additional pacing electrodes for location in the right ventricle or elsewhere. Additionally or alternatively, the lead may carry cardioversion defibrillation electrodes adapted to be located in the right ventricle, superior vena cava or coronary sinus. Preferably, the lead body distal to the fixation curves is of sufficient length to extend past the desired location of the atrial pacing electrode to the desired location of the ventricular or other pacing electrode and/or cardioversion/defibrillation electrodes.

In several embodiments discussed herein, the lead is typically implanted by first locating the right ventricular pacing electrode in its desired location and subsequently locating the atrial pacing electrode or electrodes in the superior vena cava. This may be accomplished by inserting an internal stylet to straighten the lead body and passing the lead through the vascular system until the ventricular electrode is at its desired location, thereafter withdrawing the internal stylet and moving the lead body distally to allow the fixation curves on the lead body to be displayed in the right atrium, distal to the end of the stylet. The lead may the be pulled proximally to place the atrial pacing electrodes in their desired locations in the superior vena cava. After location of the electrodes in the superior vena cava, the stylet is withdrawn completely and the lead is anchored at its site of venous insertion in connection with an implantable pulse generator in a conventional fashion. Alternatively, the lead body may be straightened by means of a guide catheter through which the lead is passed to the desired location of the ventricular pacing electrode, with the guide catheter moved proximally and the lead moved distally to allow the fixation curves to be displayed in the right atrium, followed by the lead being pulled proximally to locate the atrial pacing electrodes in the superior vena cava as discussed above. Location of the lead in embodiments in which the lead is provided with one or more electrodes for location in the coronary sinus, right atrium elsewhere may be accomplished in an analogous fashion.

DETAILED DESCRIPTION OF THE DRAWINGS

Figure 1:
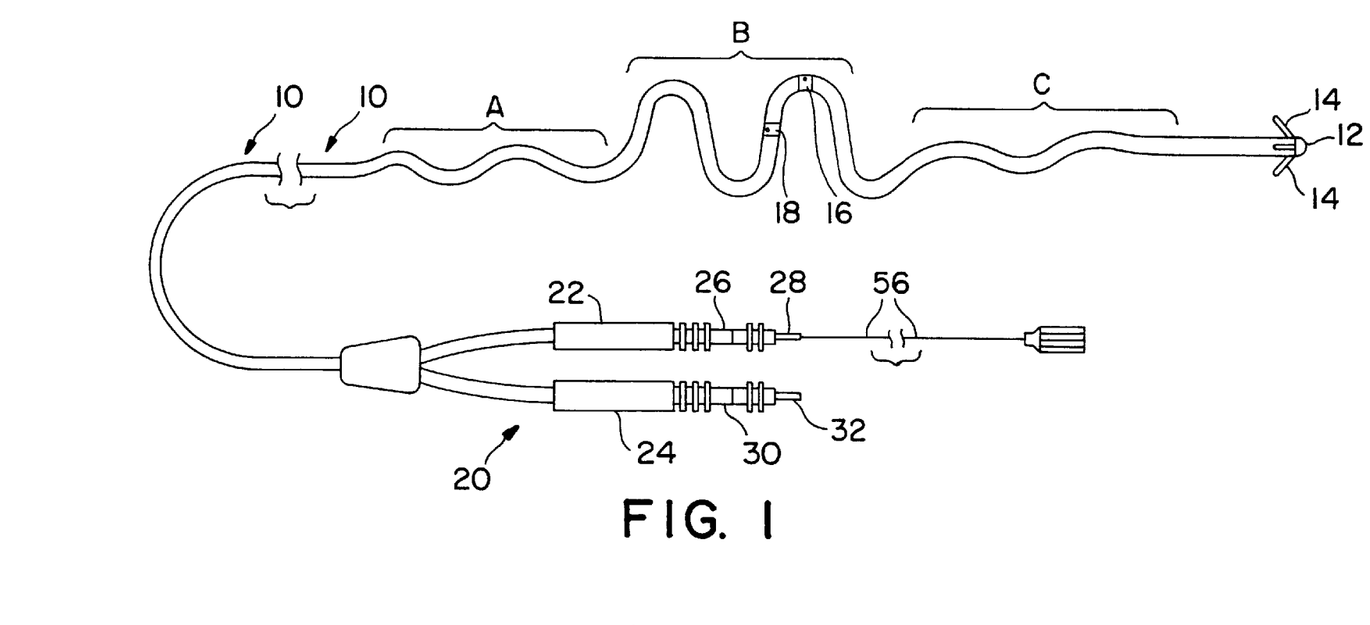
FIG. 1 is a plan view of a first embodiment of a lead according to the present invention.

FIG. 1 is a plan view of a lead according to a first embodiment of the present invention. The lead is provided with an elongated lead body 10 which may be fabricated of an insulative biocompatible plastic such as polyurethane or silicone rubber. At the distal end of the lead is a ventricular pacing electrode 12, provided with associated pliant tines 14 for assisting in maintaining the electrode in a desired location in the right ventricle in the human heart. The lead body is provided with three curved sections, A, B, and C. Curved section B is provided with a series of sigmoidal or sinusoidal fixation curves extending laterally when in a relaxed condition for a distance greater than the diameter of the superior vena cava into which the lead is intended to be implanted The fixation curves should be at least 2 cm. in lateral width, preferably 2–4 cm. Along section B of the lead are located two atrial pacing electrodes 16 and 18, electrode 16 being located on the outermost portion of one of the defined fixation curves, so that it will bear against the internal surface of the superior vena cava when deployed. Proximal and distal to curved section B are curved sections A and C, each of which are provided with a series of sigmoidal or sinusoidal stretch curves extending laterally to a lesser extent than the fixation curves associated with section B. As described above, the purpose of the stretch curves along A and C is to allow the stretching of the lead in response to the application of tensile force proximal to or distal to section B, allowing the lead to lengthen slightly rather than displacing electrodes 16 and 18 when deployed. The lead body is sized such that when the fixation curves are displayed as illustrated, the distance between the electrode 12 and the electrode 16 is greater than the typical distance from the right ventricular apex to the superior vena cava of a human heart. This distance between electrodes 12 and 16 is preferably greater than 12 cm and more preferably between 12 and 20 cm.

Curved sections A, B and C may be defined by means of heat treating one or more of the conductors within the lead body and/or by heat treating or molding the plastic of which the lead body 10 is formed to correspondingly form the desired curvature. Mechanisms appropriate for defining curves along the length of the lead body are disclosed in U.S. Pat. No. 3,729,008 issued to Berkovits, U.S. Pat. No. 4,394,866 issued to Hughes, U.S. Pat. No. 5,628,778 issued to Kruse et al. and U.S. Pat. No. 4,402,330 issued to Lindemans, all incorporated herein by reference in their entireties. In one preferred embodiment, the body of the lead 10 is fabricated of silicone rubber or polyurethane and the illustrated curvature is provided by means of a coiled conductor extending from connector pin 28 to electrode 12, which conductor has been heat treated to display the curvature illustrated.

The proximal end of the lead carries a connector portion 20 which includes two connector assemblies 22 and 24, each of which may be IS-1 type connector assemblies of the type typically employed in conjunction with implantable cardiac pacemakers and defibrillators. Connector assembly 22 is provided with a connector pin 28 which is coupled to electrode 12 at the distal end of the lead and with a metal ring 26 which in this embodiment is not coupled to any electrodes, but which in alternate embodiments would be coupled to an additional electrode such as a ventricular ring electrode or a defibrillation electrode. Connector assembly 24 is provided with a connector pin 32 coupled to electrode 16 and a connector ring 30 coupled to electrode 18.

Electrodes 16 and 18 as illustrated take the form of smooth surfaced circumferential ring electrodes. However, one or more of electrodes 16 and 18 may comprise an electrode extending less than the full circumference of the lead body as those described in U.S. Pat. No. 5,628,778 issued to Kruse or may be provided with ridges perpendicular to the axis of the lead body to reduce slippage of the electrode, also as described in U.S. Pat. No. 5,628,778 issued to Kruse. Alternatively, tines or other mechanisms for reducing slippage of the electrodes, also as disclosed in the Kruse '778 patent may also be employed adjacent electrode 16.

Tip electrode 12 is preferably a steroid eluting, porous, sintered electrode of the type described in U.S. Pat. No. 5,282,844 issued to Stokes et al. or U.S. Pat. No. 4,506,680 issued to Stokes, both incorporated herein by reference in their entireties. However, any other type of known pacing electrodes, including active fixation electrodes as described in U.S. Pat. No. 4,972,848 issued to DiDomenico et al., porous, non-drug eluting electrodes as described in U.S. Pat. No. 4,934,381 issued to MacGregor, polished metal electrodes as described in U.S. Pat. No. 4,030,508 issued to Thalen or carbon electrodes as described in U.S. Pat. No. 4,033,357 issued to Helland et al., all incorporated by reference in their entireties may alternatively be employed.

A stylet 56 is shown extending from connector pin 28. Stylet 56 is long enough to extend to the distal end of the lead body 10 and when so inserted serves to substantially straighten the curves located long sections A, B and C. When so inserted, the stylet is used to assist in advancement of the lead into the right ventricle and to position the right ventricular pacing electrode 12. As the stylet is withdrawn proximally, the curves formed in the lead body are displayed. As illustrated, the stylet 56 is withdrawn to a point proximal to curved section A so that all curves of the lead body 10 are displayed. As noted above, a guide catheter may be substituted for the stylet 56.

Figure 2:
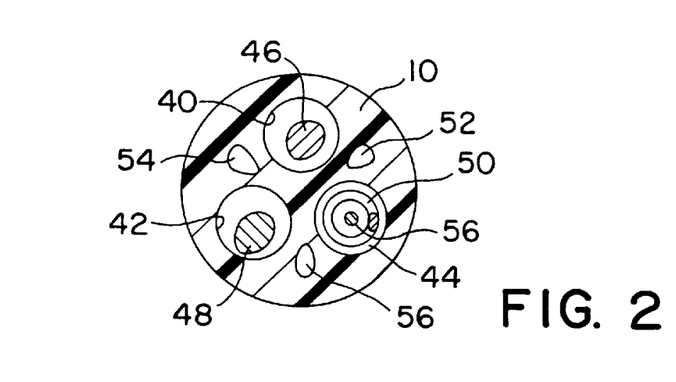
FIG. 2 is a cross-section through the body of a lead illustrated in FIG. 1.

FIG. 2 is a cross-section through the lead body 10 of the lead illustrated in FIG. 1. In this view it can be seen that the lead body corresponds to that presently employed in commercial Medtronic, Inc. implantable defibrillation leads and described in U.S. Pat. No. 5,584,873 issued to Shoberg et al. incorporated herein by reference in its entirety. The lead body is fabricated of silicone rubber, polyurethane or other implantable insulative material and is provided with three conductor lumens 40, 42 and 44, each carrying a conductor 46, 48 and 50, respectively. Conductors 46 and 48 may be bundled stranded wires or cables as described in the Shoberg et al. patent. Alternatively, coiled conductors, tinsel wire, or other known electrical conductors for use in implantable stimulation leads may be employed. Conductor 46 couples connector pin 32 to electrode 16. Conductor 48 couples electrode 18 to connector ring 30. Conductor 50 is a coiled conductor of one or more filars, extending from tip electrode 12 to connector pin 28. In the embodiment illustrated, coiled conductor 50 has been heat treated in order to cause lead body 10 to assume the configuration in FIG. 1. The lead is straightened by means of insertion of a stylet 56 down the internal lumen of coiled conductor 50, in order to straighten it and correspondingly straighten the lead. Tear drop shaped compression lumens 52, 54 and 56 are provided in order to enhance the durability of the lead, as described in the Shoberg et al. patent, discussed above. While the lead body design illustrated in FIG. 2 is believed especially suited to the fabrication of multi-conductor leads as may be employed in practicing the present invention, other multi-lumen designs and co-axial designs as disclosed in U.S. Pat. No. 5,303,704, issued to Molacek et al., U.S. Pat. No. 5,324,321, issued to Pohndorf et al. and U.S. Pat. No. 4,355,646, issued to Kallok et al., all incorporated by reference in their entireties, as well as other known lead body designs may also be employed.

While the lead illustrated in FIG. 1 is provided with three electrodes, it is within the scope of the invention to add additional electrodes. For example, a ring electrode might be added located slightly proximal to tip electrode 12, coupled by means of an additional conductor within the lead body to connector ring 26. As discussed below, defibrillation electrodes may also be added or substituted for one or more of the electrodes illustrated in FIG. 1. It should also be understood that the lead body configuration as illustrated in FIG. 2 is merely exemplary, and that the configuration of the lead body will change as a function of the number of conductors and the number of electrodes to be passed through it, correspondingly affecting the structure and number of lumens located within the lead body. In addition, it should be understood that a coaxial arrangement as is presently employed in a substantial proportion of implantable medical pacing and defibrillation presently marketed might be substituted for the multiple lumen design illustrated in FIG. 2.

Figure 3:
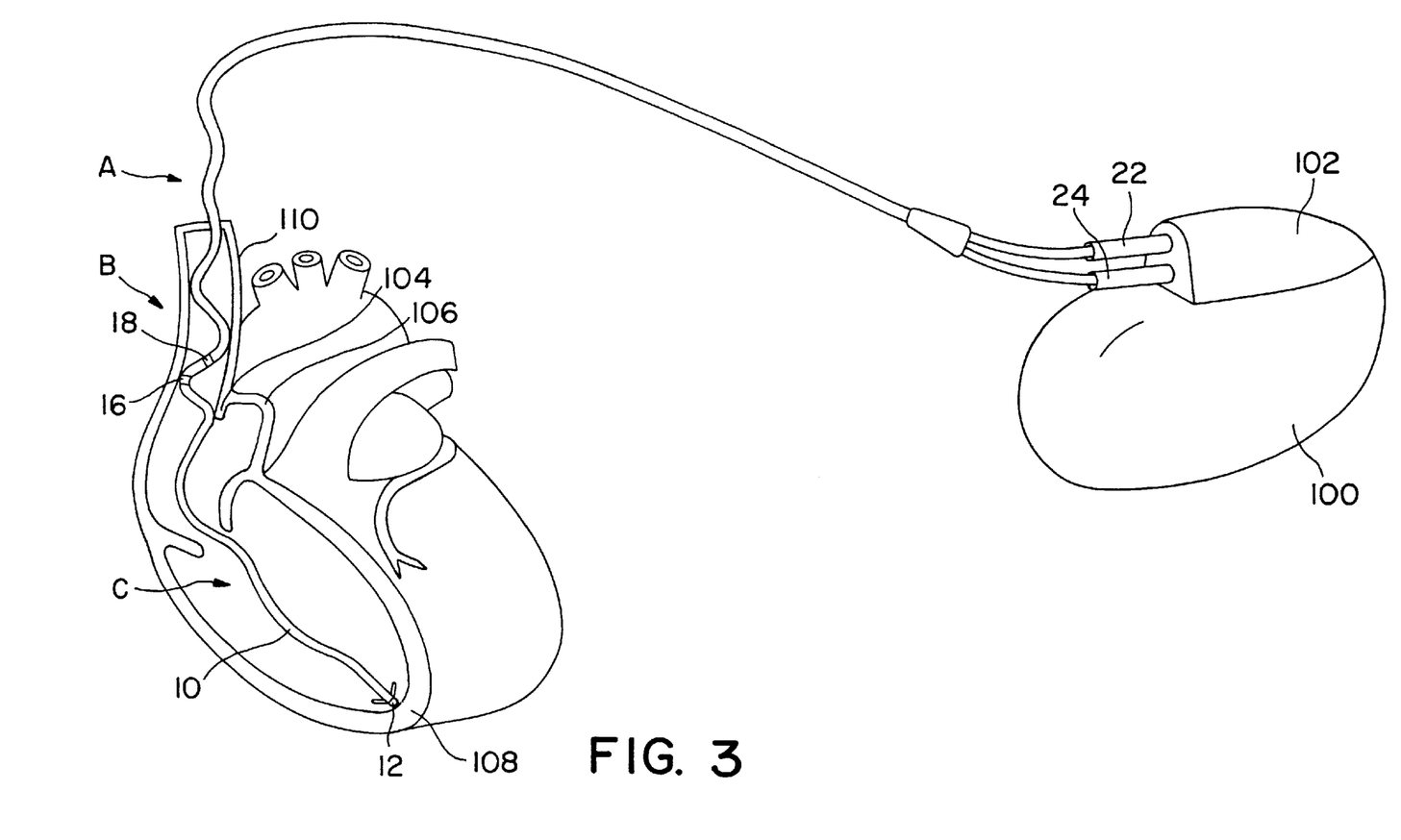
FIG. 3 is an illustration of the lead of FIGS. 1 and 2 as implanted in a human heart, and coupled to an implantable pulse generator.

FIG. 3 is an illustration of the lead of FIGS. 1 and 2 as implanted in a human heart. The tip electrode 12 is shown located in the right ventricular apex 108, with the lead body 10 passing through the tricuspid valve and the atrium such that curved portion B of the lead, carrying electrodes 16 and 18 is located in the superior vena cava 110. For purposes of the present invention, the superior vena cava may be considered to begin at the point at which the base of the crista terminae 104 intersects the wall of the right atrial appendage 106.

As installed, curved section B is located in the superior vena cava, with the lobes of the defined fixation curves engaging the walls of the superior vena cava to maintain electrode 16 in contact with the superior vena cava, above the atrium. Curved portions A and C display the stretch curves which provide for a limited amount of longitudinal stretching, to prevent displacement of electrodes 16 and 18 due to applied tensile forces to lead body 10.

In order to implant the lead of FIG. 3, the lead is first straightened by means of an internal stylet or external guide catheter which is passed along the length of the lead causing the fixation curves to be straightened. The lead is then passed through the venous system and the distal tip electrode 12 is located in the right ventricle. The stylet or guide catheter is then partially withdrawn from the lead while the lead is advanced slightly distally, such that its distal end is proximal to atrial electrodes 16 and 18 and the fixation curves are displayed in the right atrium. The lead is then pulled proximally to position atrial electrode 16 within the superior vena cava and the stylet or guide catheter is removed. The stylet or guide catheter may be employed to straighten and reposition section B of the lead within the superior vena cava, until electrodes 16 and 18 are located in a position providing acceptable pacing and sensing thresholds. After removal of the stylet or guide catheter, the lead is coupled to an implanted pulse generator 100, with connector assemblies 22 and 24 inserted into connector block 102 of the pulse generator.

Figure 4:
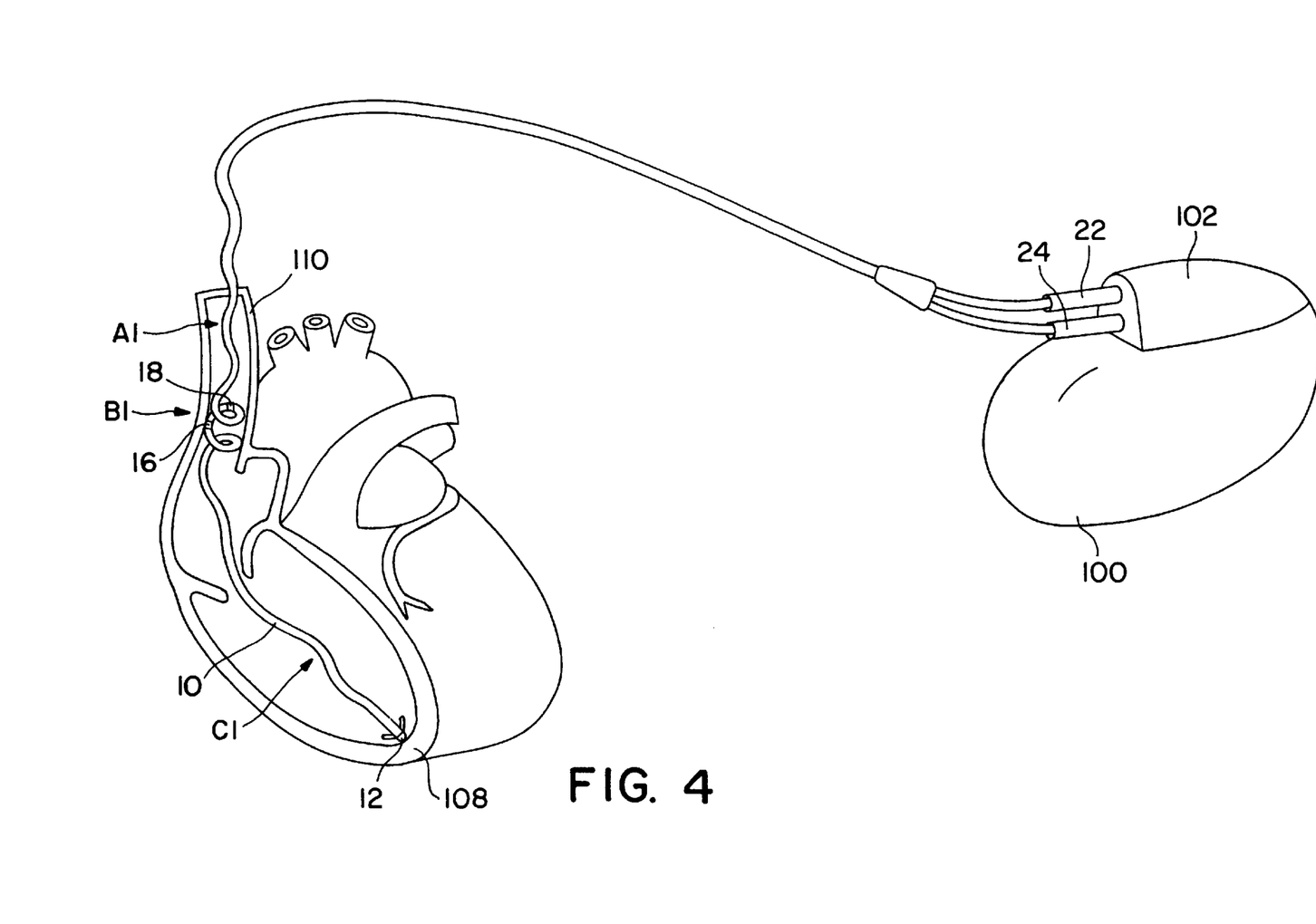
FIG. 4 is a view of a second embodiment of a lead according to the present invention, implanted in a human heart and coupled to an implantable pulse generator.

FIG. 4 illustrates a second embodiment of a lead according to the present invention. In this embodiment, all structures correspond to identically numbered structures illustrated in FIGS. 1–3, with the exception that fixation curves located along curved portion B1 of the lead, instead of taking the form of sigmoidal or sinusoidal curves, take the form of a spiral, with ring electrodes 16 and 18 located along the spiral. The spiral curve is sized so that when relaxed, it extends laterally for a distance greater than the diameter of the superior vena cava into which it is to be implanted, so that the spiral configuration can maintain electrodes 16 and 18 located adjacent the wall of the superior vena cava. Curved sections A1 and C1 correspond to curved sections A and B illustrated in FIG. 1. The lead is implanted in the same manner as the lead illustrated in FIGS. 1–3, and otherwise corresponds to the lead illustrated in FIGS. 1–3.

Figure 5:
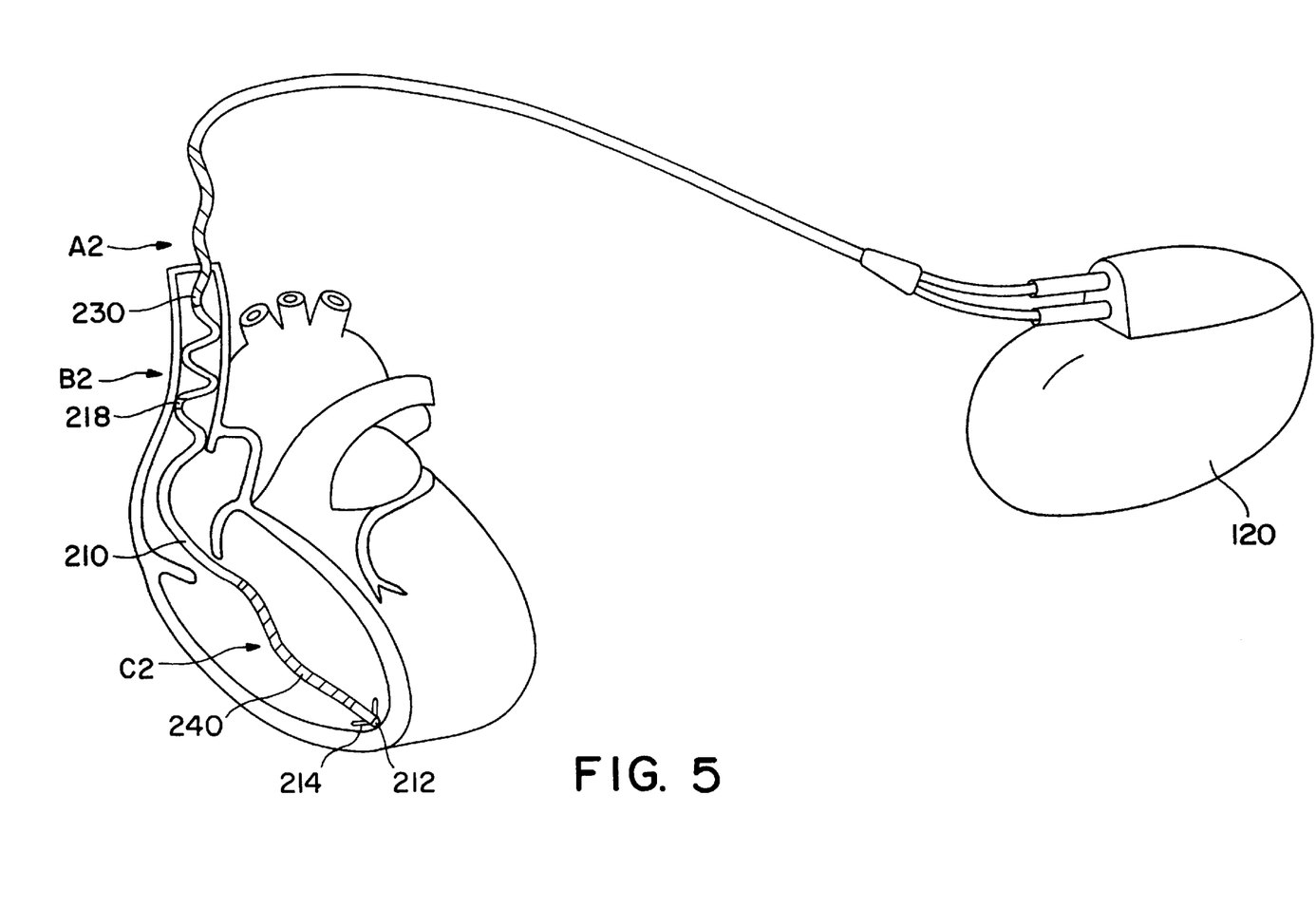
FIG. 5 is a view of a third embodiment of a lead according to the present invention, implanted in a human heart and coupled to an implantable pulse generator.

FIG. 5 illustrates a third embodiment of a lead according to the present invention implanted in the human heart. In this embodiment only a single electrode 218 is provided on curved segment B, and defibrillation electrodes 230 and 240 are located proximal and distal, respectively to curved section B2. As illustrated, electrodes 230 and 240 are located along curved sections A2 and C2, with a ventricular pacing electrode 212 and associated tines 214, located at the distal end of the lead body 210. The lead is implanted and deployed precisely as described above in conjunction with the lead illustrated in FIGS. 1 and 2. The lead body 210 differs from the lead body 10 of the leads in FIGS. 1–4 in that it carries four internal conductors rather than three internal conductors. The lead is implanted in the same manner as the lead illustrated in FIGS. 1–3. The lead is connected to an implantable pacemaker/cardioverter/defibrillator 120.

Figure 6:
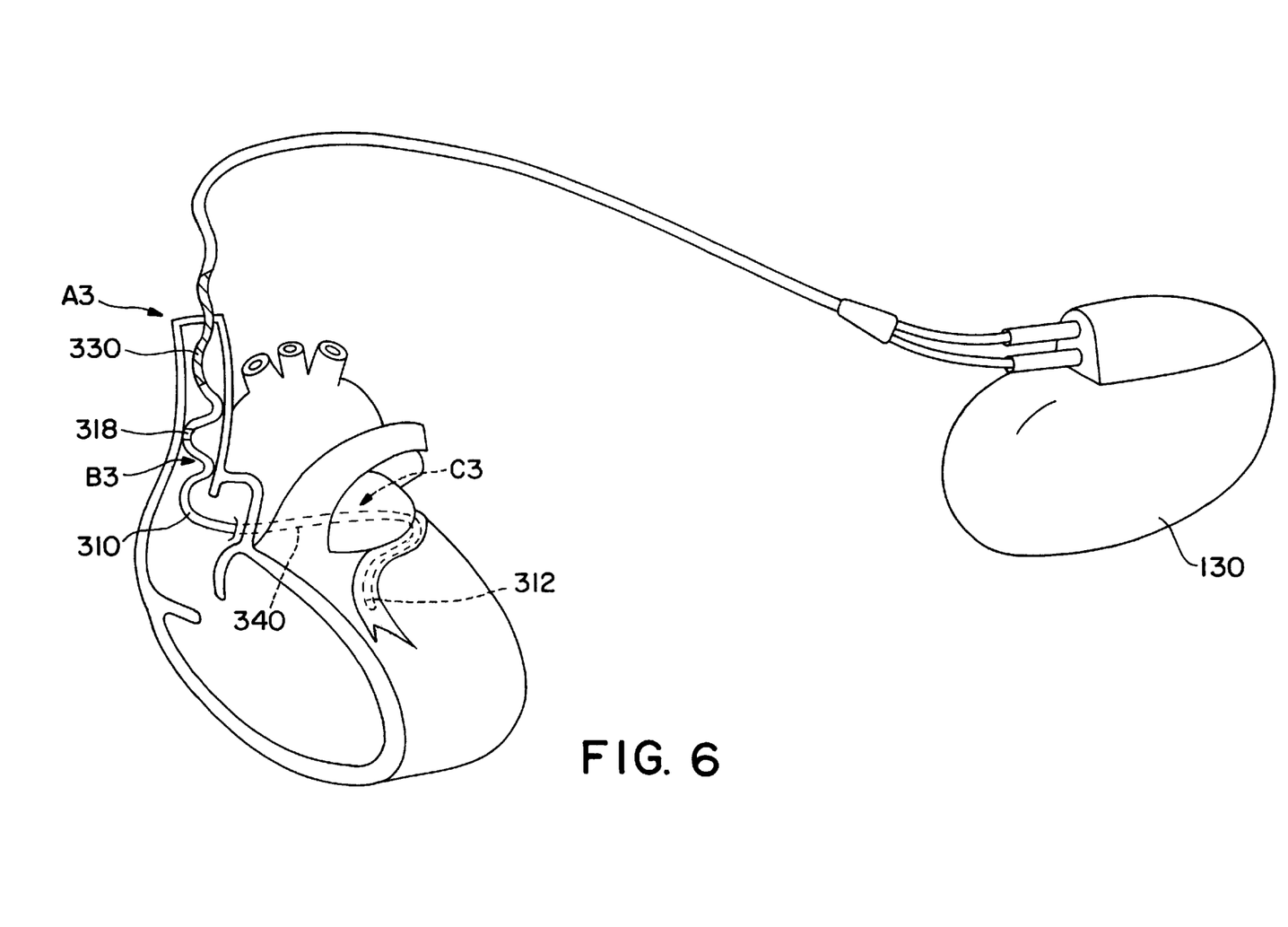
FIG. 6 is a fourth embodiment of a lead according to the present invention, implanted in a human heart and coupled to an implantable pulse generator.

FIG. 6 illustrates a fourth embodiment of a lead according to the present invention, corresponding generally in structure to the lead illustrated in FIG. 5, modified by removal of tines 214 (FIG. 5) and by reducing the diameter of the lead body 310 to allow it to be advanced into the coronary sinus and great vein of the heart. Defibrillation electrode 330 and atrial pacing electrode 318 correspond to electrodes 230 and 218 illustrated in FIG. 5. The distal portion of the lead carrying tip electrode 312 and defibrillation electrode 340 is indicated in broken outline, located such that the tip electrode 312 is adjacent the left ventricle and the defibrillation electrode 340 is adjacent the left atrium in the coronary sinus. Curved sections A3 and B3 correspond to curved sections A2 and B2 illustrated in FIG. 5. Section C3, along which defibrillation electrode 340 is located may be constructed to display a sigmoidal curve both to allow stretch and to assist in fixing the lead in the coronary sinus. This embodiment may be particularly valuable for use in conjunction with implantable atrial cardioverter or defibrillator 130, which may be of the type described in described in U.S. Pat. No. 5,269,298 issued to Adams et al, with the lead substituted for the lead disclosed therein. In this embodiment, the lead body would carry four conductors, rather than three conductors as in the preceding embodiments. The lead is introduced by advancing the distal end of the lead into the coronary sinus and great cardiac vein to the desired point, withdrawing the stylet or guide catheter deploying the curved section B3 as described above to locate electrodes 16 and 18 in the superior vena cava and withdrawing the stylet or guide catheter entirely prior to coupling the lead to an implanted defibrillator 200, as illustrated.

In an alternative embodiment, the defibrillation electrode 340 may be removed and the lead length adjusted so that so that electrode 312 is located adjacent the left atrium or more proximally. In this embodiment the lead may be used for multi-site atrial pacing and may be coupled to a single or dual chamber pacemaker.

Figure 7:
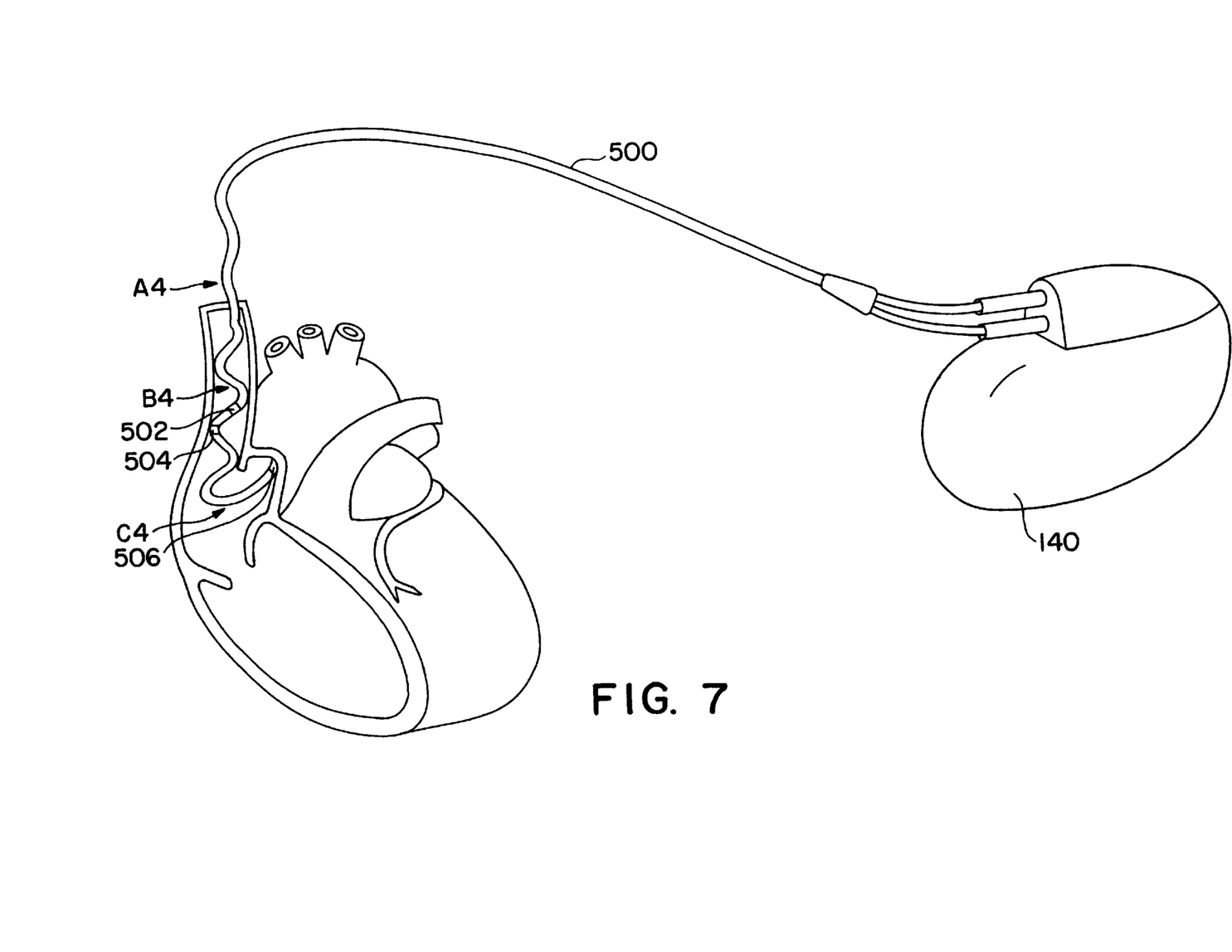
FIG. 7 is a fourth embodiment of a lead according to the present invention, implanted in a human heart and coupled to an implantable pulse generator.

FIG. 7 illustrates a fifth embodiment of a lead 500 according to the present invention, corresponding generally in structure to the lead illustrated in FIG. 1, modified by substitution of a "J" shaped curved section C4 for the stretch curves C of the lead of FIG. 1. This embodiment of the invention is intended to be employed as a multi-site atrial pacing lead, with tip electrode 506 located in the right atrial appendage. Curved sections A4 and B4 correspond to curved sections A and B illustrated in FIG. 1, with electrodes 502 and 504 corresponding to electrodes 16 and 18. The lead is shown coupled to an atrial pacemaker 140.

Figure 8:
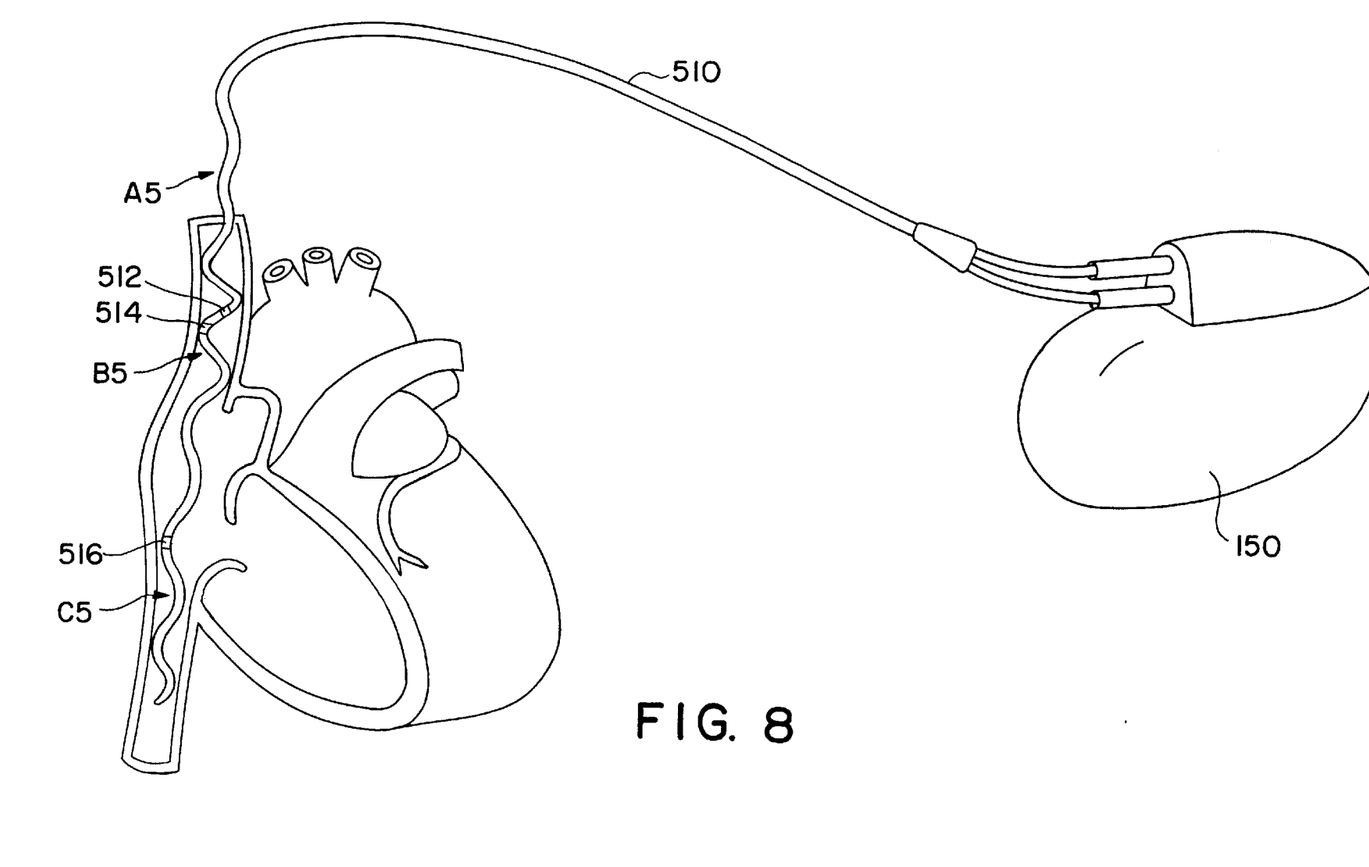
FIG. 8 is a fourth embodiment of a lead according to the present invention, implanted in a human heart and coupled to an implantable pulse generator.

FIG. 8 illustrates a sixth embodiment of a lead 510 according to the present invention, corresponding generally in structure to the lead illustrated in FIG. 1, modified by increasing the lateral extension of the curves along section C5 of the lead as compared to the stretch curves C of the lead of FIG. 1 so that they may be employed as fixation curves for locating the distal section of the lead in the inferior vena cava and by movement of the electrode 516 proximal to the distal end of the lead. This embodiment of the invention is also intended to be employed as a multi-site atrial pacing lead, with electrode 516 located in the right atrium or inferior vena cava. Curved sections A5 and B5 correspond to curved sections A and B illustrated in FIG. 1, with electrodes 512 and 514 corresponding to electrodes 16 and 18. The lead is shown coupled to an atrial pacemaker 150.

Figure 9:
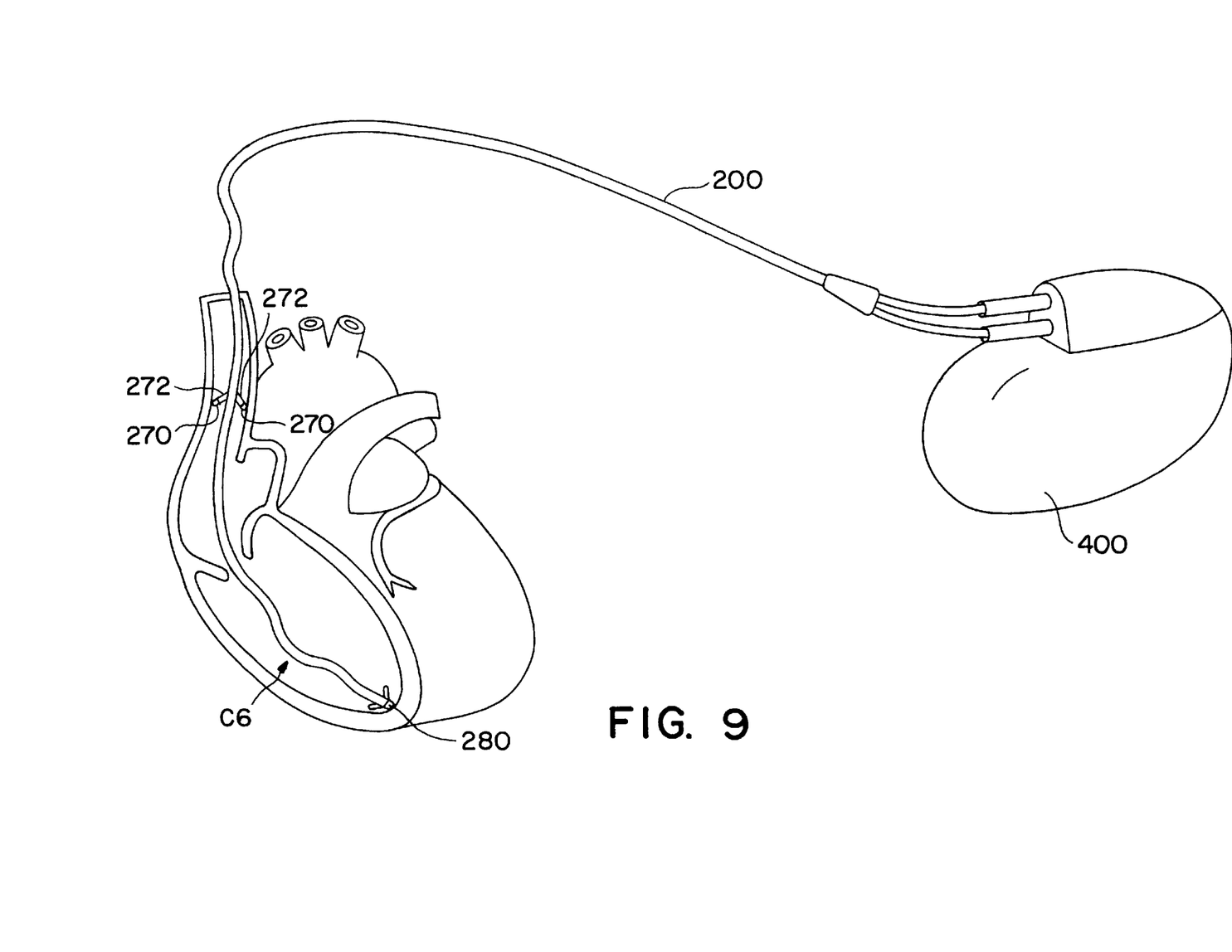
FIG. 9 is a plan view of a lead employing electrodes located on extending tines or arms, for location in the superior vena cava, as implanted in the human heart and coupled to an implantable pulse generator.

FIG. 9 illustrates the implantation of a lead employing atrial electrodes 270 located on outwardly extending tines or arms 272 in conjunction with the method of implantation described above. The lead may correspond generally to that illustrated in U.S. Pat. No. 4,386,615 issued to Sowton, incorporated herein by reference in its entirety. The lead extends distally from tines 272 to a tip electrode 280. Preferably, the length of the lead body between tines 272 and tip electrode 280 is greater than the distance from the lower portion of the superior vena cava to the right ventricular apex, in order that the lead may display slack when implanted. Alternatively or in addition, portion C6 of the lead may be provided with stretch curves, as discussed above in conjunction with the leads illustrated in FIGS. 1–6. The lead is implanted by advancing the distal end of the lead by means of an internal stylet which is thereafter withdrawn proximally to allow positioning of the electrodes 280 at a desired location within the superior vena cava. The stylet is then withdrawn and the lead is connected to an implantable pulse generator 400.

Figure 10:
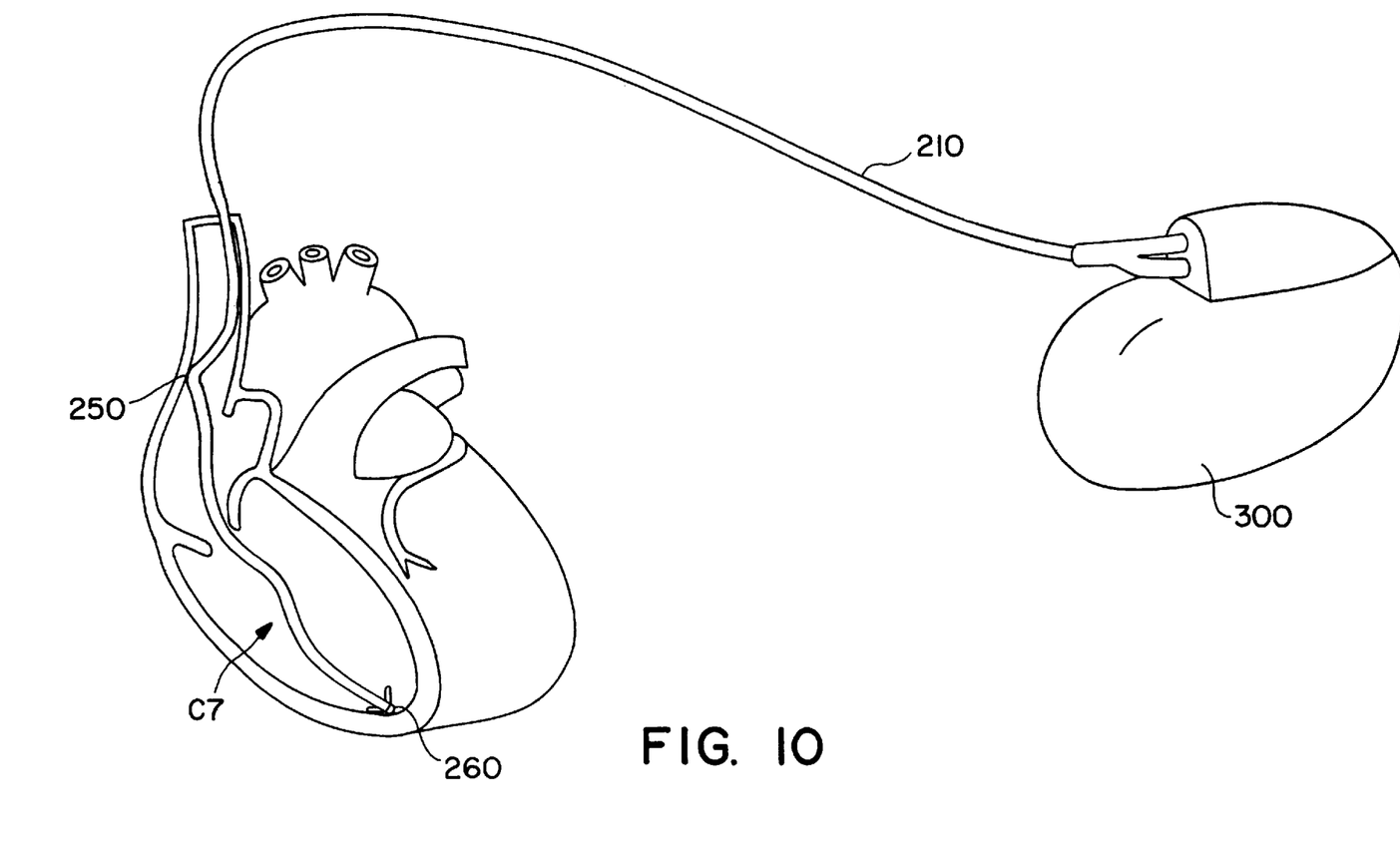
FIG. 10 is a figure of a lead employing an active fixation mechanism for location of an atrial pacing electrode in the superior vena cava, as implanted in a human heart and coupled to an implantable pulse generator.

FIG. 10 illustrates a lead 210 employing an active fixation device which may also be used according to the method of implantation described above. The lead is provided with an advanceable barb or hook electrode 250, according to U.S. Pat. No. 4,497,326 issued to Curry, incorporated herein by reference in its entirety. Extending distally from hook or barb 250, the lead carries a distal tip electrode 260, located in the right ventricular apex. In use, the lead is implanted by first advancing the distal end of the lead to the right ventricular apex by means of an internal stylet which is thereafter withdrawn in order to allow positioning of the electrode 250 at a desired location in the superior vena cava. The electrode 250 is then advanced out of the lead body and engaged with the wall of the superior vena cava prior to connection of the lead to an implantable pacemaker 300. The length from electrode 250 to the distal electrode 260 is preferably greater than the distance from the lower portion of the superior vena cava to the right ventricular apex so that the lead as implanted exhibits some slack. Alternatively or in addition, the distal portion C7 of the lead may be provided with stretch curves as discussed in conjunction with the embodiments illustrated above.

In conjunction with the above disclosure, we claim:

1. A method of pacing a right atrium of a patient's heart, comprising:

advancing an electrode lead having a first electrode located on a distal portion of the lead and having a second electrode located proximal to the first electrode and having means for affixing the second electrode adjacent a wall of the patient's superior vena cava by passing the first electrode through the right atrium of the patient's heart to a desired location outside the right atrium;

employing the affixing means to affix the second electrode in the patient's superior vena cava adjacent a wall of the patient's superior vena cava; and pacing the right atrium of the patient's heart through the second electrode.

2. A method according to claim 1 wherein said advancing step comprises advancing the lead having a lead body formed to display a curvature extending laterally over a width sufficient to span a human superior vena cava and having said second electrode located on a laterally extending portion of said curvature and wherein employing step comprises locating said curvature such that the second electrode is located adjacent the wall of the superior vena cava.

3. A method according to claim 1 wherein said advancing step comprises advancing the lead having an active fixation mechanism associated with said second electrode and wherein employing step comprises employing said active fixation mechanism to locate the second electrode adjacent the wall of the superior vena cava.

4. A method according to claim 1 wherein said advancing step comprises advancing the lead having a laterally extending member and having said second electrode located on said laterally extending member and wherein employing step comprises employing laterally extending member said to locate the second electrode adjacent the wall of the superior vena cava.

5. A method of pacing a right atrium of a patient's heart, comprising:

advancing an electrode lead having a first electrode located on a distal portion of the lead and having a second electrode located proximal to the first electrode and having a lead body with a curvature extending laterally over a width sufficient to span a human superior vena cava and having said second electrode located on a laterally extending portion of said curvature by passing the first electrode through the right atrium of the patient's heart to a desired location outside the right atrium;

affixing the second electrode in the patient's superior vena cava adjacent a wall of the patient's superior vena cava by locating said curvature such that the second electrode is located adjacent the wall of the superior vena cava; and pacing the right atrium of the patient's heart through the second electrode.

6. A method of pacing a right atrium of a patient's heart, comprising:

advancing an electrode lead having a first electrode located on a distal portion of the lead and having a second electrode located proximal to the first electrode and having an active fixation mechanism associated with the second electrode by passing the first electrode through the right atrium of the patient's heart to a desired location outside the right atrium;

employing the active fixation mechanism to affix the second electrode in the patient's superior vena cava adjacent a wall of the patient's superior vena cava; and pacing the right atrium of the patient's heart through the second electrode.

7. A method of pacing a right atrium of a patient's heart, comprising:

advancing an electrode lead having a laterally extending member and having a first electrode located on a distal portion of the lead and having a second electrode located on said laterally extending member proximal to the first electrode by passing the first electrode through the right atrium of the patient's heart to a desired location outside the right atrium;

employing the laterally extending member said to locate the second electrode in the patient's superior vena cava adjacent a wall of the patient's superior vena cava; and pacing the right atrium of the patient's heart through the second electrode.

8. A method according to claim 1 or claim 5 or claim 6 or claim 7, further comprising the step of locating the first electrode in the patient's right ventricle.

9. A method according to claim 1 or claim 5 or claim 6 or claim 7, further comprising the step of locating the first electrode in the patient's coronary sinus.

10. A method according to claim 1 or claim 5 or claim 6 or claim 7, further comprising the step of locating the first electrode in the patient's right atrium.

\* \* \* \* \*